United States Patent [19]

Meares et al.

[11] Patent Number: 4,678,667
[45] Date of Patent: Jul. 7, 1987

[54] MACROCYCLIC BIFUNCTIONAL CHELATING AGENTS

[75] Inventors: Claude F. Meares, Davis; Sally J. DeNardo, El Macero, both of Calif.; William C. Cole, Houston, Tex.; Min K. Mol, Davis, Calif.

[73] Assignee: 501 Regents of the University of California, Berkeley, Calif.

[21] Appl. No.: 751,769

[22] Filed: Jul. 2, 1985

[51] Int. Cl.$^4$ ............ A61K 39/00; A61K 39/42; A61K 43/00; A61K 49/00
[52] U.S. Cl. ............ 424/85; 540/465; 424/9
[58] Field of Search ........... 424/85; 260/112, 112.5 R, 260/239 BC

[56] References Cited

U.S. PATENT DOCUMENTS 4,472,509 9/1984 Gansow et al. .............. 424/85

OTHER PUBLICATIONS

Tabushi, I., et al, *Tetrahedron Letters* (1977), 12:1049.
Delgado, R., et al, *Talanta* (1982), 29:815.
Stetter, H., et al, *Tetrahedron Letters* (1981), 37:767.
Bearn, A. B., et al, *Proc. Soc. Exp. Biol. Med.* (1954), 85:44.
Leung, C. S.-H., et al, *International J. Applied Radiation and Isotopes* (1978), 29:687.
Meares, C. F., et al, *Anal. Biochem.* (1984), 142:68.
Meares, C. F., et al, *Accts. Chem. Res.* (1984), 17:202.

*Primary Examiner*—Ronald W. Griffin
*Attorney, Agent, or Firm*—Ciotti & Murashige, Irell & Manella

[57] ABSTRACT

A copper chelate conjugate which is stable in human serum. The conjugate includes the copper chelate of a cyclic tetraaza di-, tri-, or tetra-acetic acid, a linker attached at one linker end to a ring carbon of the chelate, and a biomolecule joined at the other end of the linker. The conjugate, or the linker-copper chelate compound used in forming the conjugate, are designed for use in diagnostic and therapeutic applications which involve Cu(II) localization via the systemic route.

14 Claims, 4 Drawing Figures

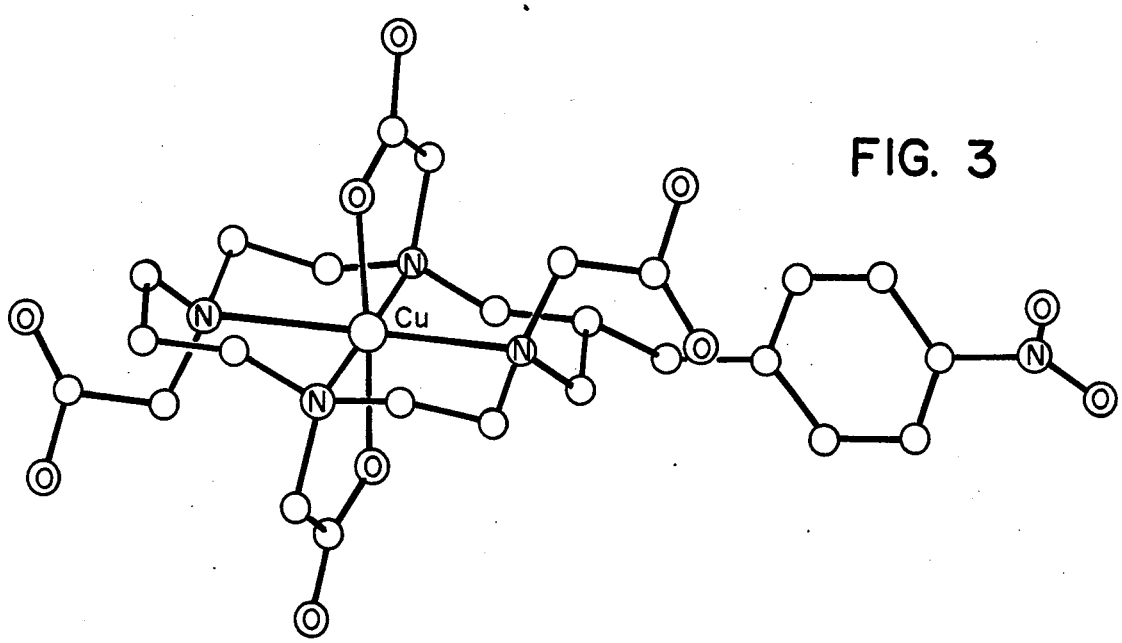
FIG. 3
FIG. 4
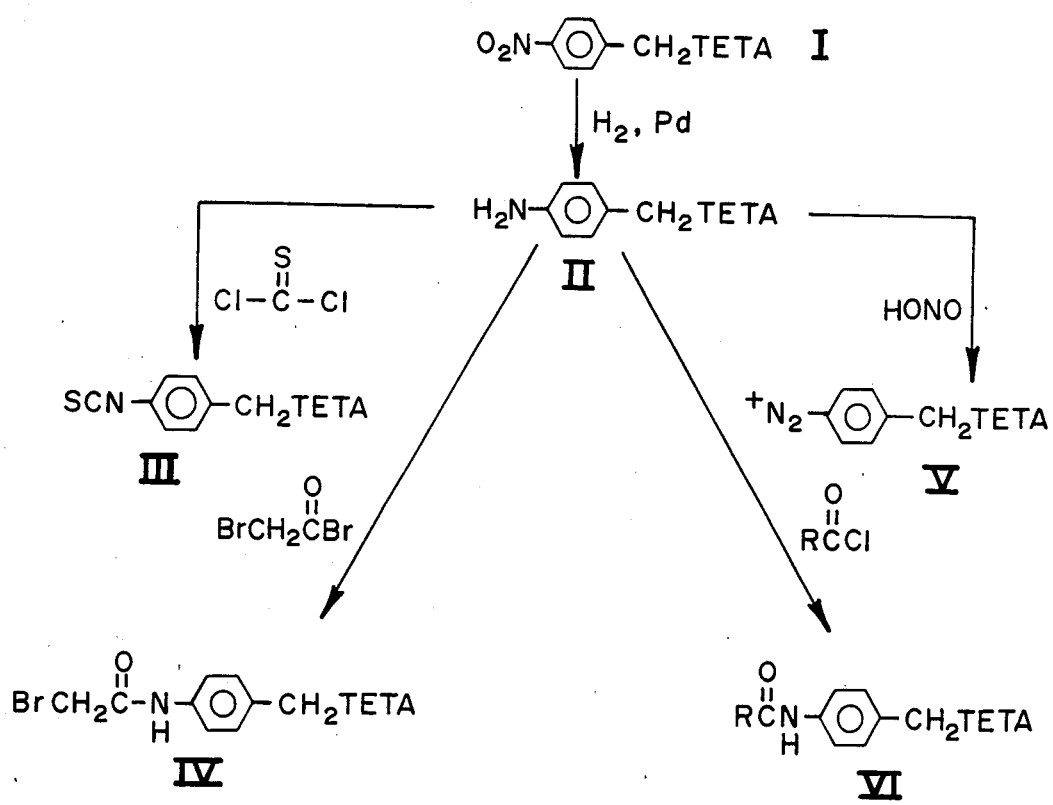

MACROCYCLIC BIFUNCTIONAL CHELATING AGENTS

BACKGROUND OF THE INVENTION

The present invention relates to copper chelating compounds which are stable in human serum.

REFERENCES

The following references are referred to herein by corresponding number:

1. Meares, et al, *Accts Chem Res* (1984) 17:202.
2. DeNardo, S. J., et al, *The Developing Role of Short-lived Radionuclides in Nuclear Medicine Practice* (Paras, P., et al, eds) U.S. Dept of Energy, Washington, D.C. (1984) pp 399–412.
3. Bertini, I., et al, *Metal Ions in Biological Systems*, Vol 12 (Sigel, H., ed) M. Dekker, N.Y., (1981) pp 31–74.
4. Hanaki, A., et al, *Chem Pharm Bull* (1978) 26:325.
5. Meares, C. F., et al, *Anal Biochem* (1984) 142:68.
6. Goodwin, D. A., et al, *Radiopharmaceuticals II, Proceedings of the Second International Symposium on Radiopharmaceuticals* (Sodd, V. J., ed) N.Y. (1979) pp 275–284.
7. De Riemer, L. H., et al, *J Lab Comps and Radiopharm* (1981) 18(10):1517.
8. Meares, C. F., et al, *Proc Natl Acad Sci (USA)* (1976) 73(11):3803.
9. Leung, C. S. -H., et al, *Int J Appl Rad Isot* (1978) 29:687.
10. Goodwin, D. A., et al, *J Nuc Med* (1981) 22(9):787.
11. Bearn, A. B., et al, *Proc Soc Exp Biol Med* (1954) 85:44.
12. Hnatowich, D. J., et al, *Science (Washington, D.C.)* (1983) 220:613.
13. Tabushi, I., et al, *Tetrahedron Lett* (1977) 12:1049.
14. Delgado, R., et al, *Talanta* (1982) 29:815.
15. Stetter, H., et al, *Tetrahedron* (1981) 37:767.
16. Kohler, B., et al, *Nature* (1975) 256:495.
17. *Monoclonal Antibodies* (Kennett, T. J., et al, eds) (1980) Plenum Press.
18. Umezawa, H., *Pure Appl Chem* (1970) 28:665.
19. Fujii, A. J., *Antibiot* (1973) 26:398.
20. Yeh, S. M., et al, *J Radioanalyt Chem* (1979) 53:327.8
21. Martell, A. E., et al, *Critical Stability Constants* Vol I, (1974) Plenum, N.Y., pp 204–285.
22. Zuberbuhler, A., *Copper Coordination Chemistry: Biochemical and Inorganic Perspectives* (Karlin, K. D., et al, ed) Adenine Press, Guilderland, N.Y. (1983) pp 273–258.
23. Vogel, A. I., *Practical Organic Chemistry* (1966) Wiley, N.Y., pp 485–486.
24. Silverstein, R. M., et al, in *Spectrometric Identification of Organic Compounds* (Fourth ed.) Wiley, N.Y., (1981), pp 249–304.
25. Hafliger, H., et al, *Helv Chim Acta* (1979) 62:683.
26. Sabatini, L., et al, *J Inorganic Chem* (1979) 18(2):438.
27. Richman, J. E., et al, *J Am Chem Soc* (1974) 93:7, p 2268.
28. Richman, J. E., et al, *J Am Chem Soc* (1974) 96(7):2268.

BACKGROUND AND SUMMARY

Transition metals such as copper possess nuclear, electronic and chemical properties which are potentially useful for both diagnostic and therapeutic applications in medicine (reference 1). Copper radiosotopes have excellent properties for medical applications (reference 2), and paramagnetic copper (II) has characteristic magnetic resonance spectra which might be exploited in NMR diagnostic techniques (reference 3). Copper chelate complexes can catalyze oxidative chemical reactions (reference 4) and may therefore be useful in cancer therapy (involving for example, oxidative destruction of DNA in tumor cells).

The ability to attach metal chelate compounds to proteins, such as antibodies (reference 5), or to tumor-selective biomolecules, such as bleomycin (references 6 and 7) can lead to probe or diagnostic conjugates which can locate or inactivate specific target sites in biological systems. Typically, such a chelate/biomolecule conjugate is prepared from a bifunctional chelate compound having a metal-chelating functional moiety and a reactive linker, by which the compound is coupled to a selected molecule.

The usefulness of bifunctional metal-chelate compounds and chelate conjugates in medical applications has been shown for a number of metals, including indium, cobalt, and iron (references 1, 2, 5–10). However, it is well known that copper binds readily to serum components, such as serum albumin (reference 11). Experiments conducted in support of the present applications show that bifunctional chelating agents based on ethylenediaminetetraacetic acid (EDTA) or diethylenetriaminepentaacetic acid (DTPA) rapidly lose copper in human serum.

SUMMARY OF THE INVENTION

It is therefore an important object of the invention to provide a bifunctional copper chelate compound which is substantially stable in human serum.

A related object of the invention is to provide such a compound which, when conjugated to a suitable targeting biomolecule, can be used to target copper to a body site.

The invention includes a copper-chelate conjugates composed of a copper chelate of a macrocyclic polyamine containing four substantially planar-symmetrical ring amines, at least two of which have pendant acetic acid groups, a linker attached at one end to a ring carbon of the polyamine, and a biomolecule joined to the polyamine through the linker. An exemplary macrocyclic polyamine is 1,4,8,11 tetraazacyclotetradecane-N,N',N",N"'-tetraacetic acid.

The linker preferably includes, before conjugation, a free-end nitrobenzene group which can be reduced and activated for coupling to a biomolecule through an amide, azo, thiourea, thioether, or disulfide linkage. The biomolecule may include antibodies or antibody fragments, serum proteins or tumor-specific targeting agents, such as bleomycin.

Also forming part of the invention are methods for preparing Cu(II) for use in diagnostic and therapeutic applications which involve Cu(II) localization via the systemic route, and for using the Cu(II) chelate compound and conjugate in such applications.

These and other objects and features of the invention will become more fully apparent when the following detailed description of the invention is read in conjunction with the accompanying figures.

BRIEF DESCRIPTION OF THE DRAWINGS

FIG. 3 shows the three dimensional structure of a Cu(II) chelate complex in the invention; and FIG. 4 illustrates the reduction of the nitro group in the compound of FIG. 1, and conversion of the resulting amine to one of a variety of chemically reactive groups.

DETAILED DESCRIPTION OF THE INVENTION

I. Preparing the Bifunctional Chelate Compound

The stable copper chelate conjugate of the invention includes a copper chelate of a macrocyclic polyamine and a biomolecule joined through a linker to a ring carbon of the polyamine. The macrocyclic polyamine has the general form:

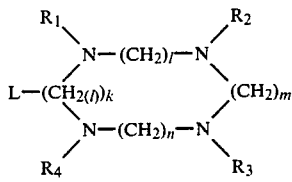

where k, l, m, n, = 1-4, and at least two of the $R_1$–$R_4$ groups are acetate groups, and where "$CH_{2(l)}$" refers to the fact that the carbon to which L is attached has only one hydrogen. A linker group L attached to a ring carbon of the macrocycle is used in coupling the chelate to the bimolecule, as will be described in Section II below. The macrocyclic polyamine and the attached linker group form a bifunctional chelate compound—so-called because of the chelate functionality provided by the polyamine and the chemical-linkage functionality provided by the linker group.

Figure 1:
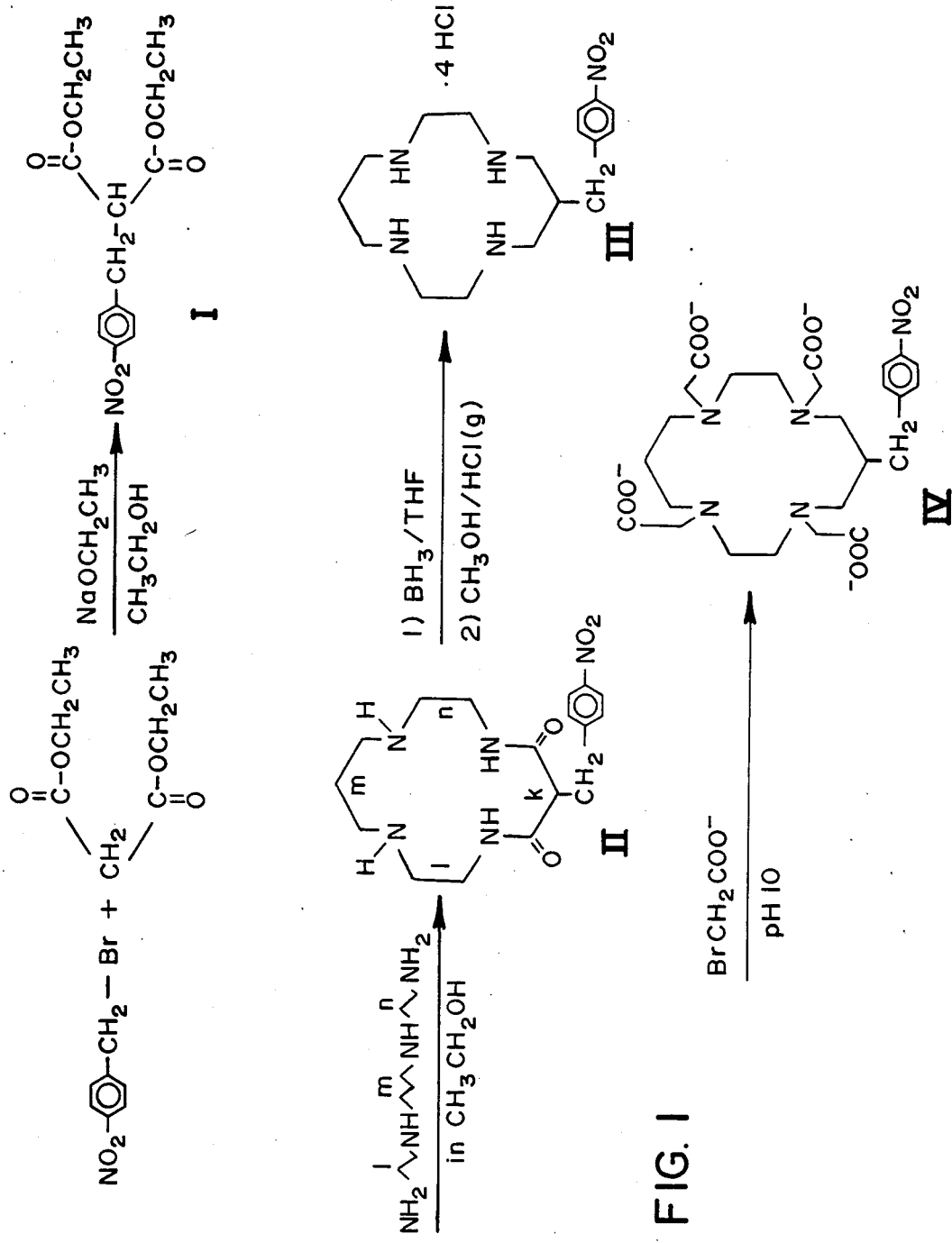
FIG. 1 shows a series of reactions used in synthesizing a bifunctional chelate compound for use in the invention.

One reaction scheme for synthesizing a bifunctional chelating compound of the above type is shown in FIG. 1. As a first step, diethylmalonate is reacted with an alkylating agent which will form the linker in the bifunctional compound. The alkylating agent terminates at its free end (after alkylation) in a structure which can later be converted into a variety of chemical reagents, which react with groups such as sulfhydryl, hydroxy, phenol, thioether, imidazole, carboxy, or amino. A variety of chain lengths and compositions are suitable. One preferred alkylating agent is p-nitrobenzylbromide (FIG. 1) whose free-end nitrobenzene group permits a number of activation reactions (described in Section II) useful in coupling biomolecules to the bifunctional compound. The alkylation reaction is carried out according to procedures detailed in Example 1. The nitrobenzyl reaction product, indicated at I in FIG. 1, may be crystallized by evaporation from a suitable solvent, and its structure confirmed by standard techniques, such as thin layer chromatography and infrared and NMR spectroscopy.

The alkylated diethylmalonate is reacted with a tetraamine compound which preferably has the form $NH_2(CH_2)_lNH_2(CH_2)_mNH_2(CH_2)_nNH_2$ where l, m, n=1–4. The l=2, m=3, n=2 tetraamine compound is illustrated in FIG. 1. The reaction is carried out by refluxing in ethanol, substantially according to the procedure described in reference 13, and detailed in Example I. The compound formed by the condensation reaction is a cyclic diamide whose linker moiety is attached to a ring carbon between the two amide linkages, as shown. The cyclic diamide product formed by reaction with the l=2, m=3, n=2 tetraamine is shown at II in the figure. The product may be purified by crystallization and further purified by silica gel column chromatography. Purification and characterization of the k=3, l=2, m=3, n=2 cyclic diamide by thin layer chromatography and IR and NMR spectroscopy is described in Example I. The cyclic diamide is reduced to the corresponding macrocyclic tetraamine compound by reduction with borane ($BH_3$) in tetrahydrofuran (THF). The reduced compound is shown at III in FIG. 1.

The macrocyclic tetraaza compound is then reacted with bromo- or chloro-acetate to form a bifunctional cyclic tetraaza tetraacetic acid chelate compound, such as the tetraacetic acid compound shown at IV FIG. 1. The chelate moiety of the bifunctional compound corresponding to the 13(ane)$N_4$ compound (k=3; l, m, n=2 is referred to as 1,4,7,10-tetraazacyclo-TRIdecane-N,N',N'',N'''-Tetra-acetic Acid (TRITA); to the 14(ane)$N_4$ compound (k=3, l=2, m=3, n=2), as 1,4,8,11-tetraaazacyclo-TEtra-decane-N,N',N'',N'''-Tetraacetic Acid (TETA) (compound IV in FIG. 1); and to the 16(ane)$N_4$ compound (k, l, m, n=3), as 1,5,9,13-tetraazacyclo HExa decane-N,N',N'',N'''-Tetraacetic Acid (HETA). The corresponding bifunctional compounds are referred to as p-nitrobenzyl-TRITA, -TETA, and -HETA, respectively.

Figure 2:
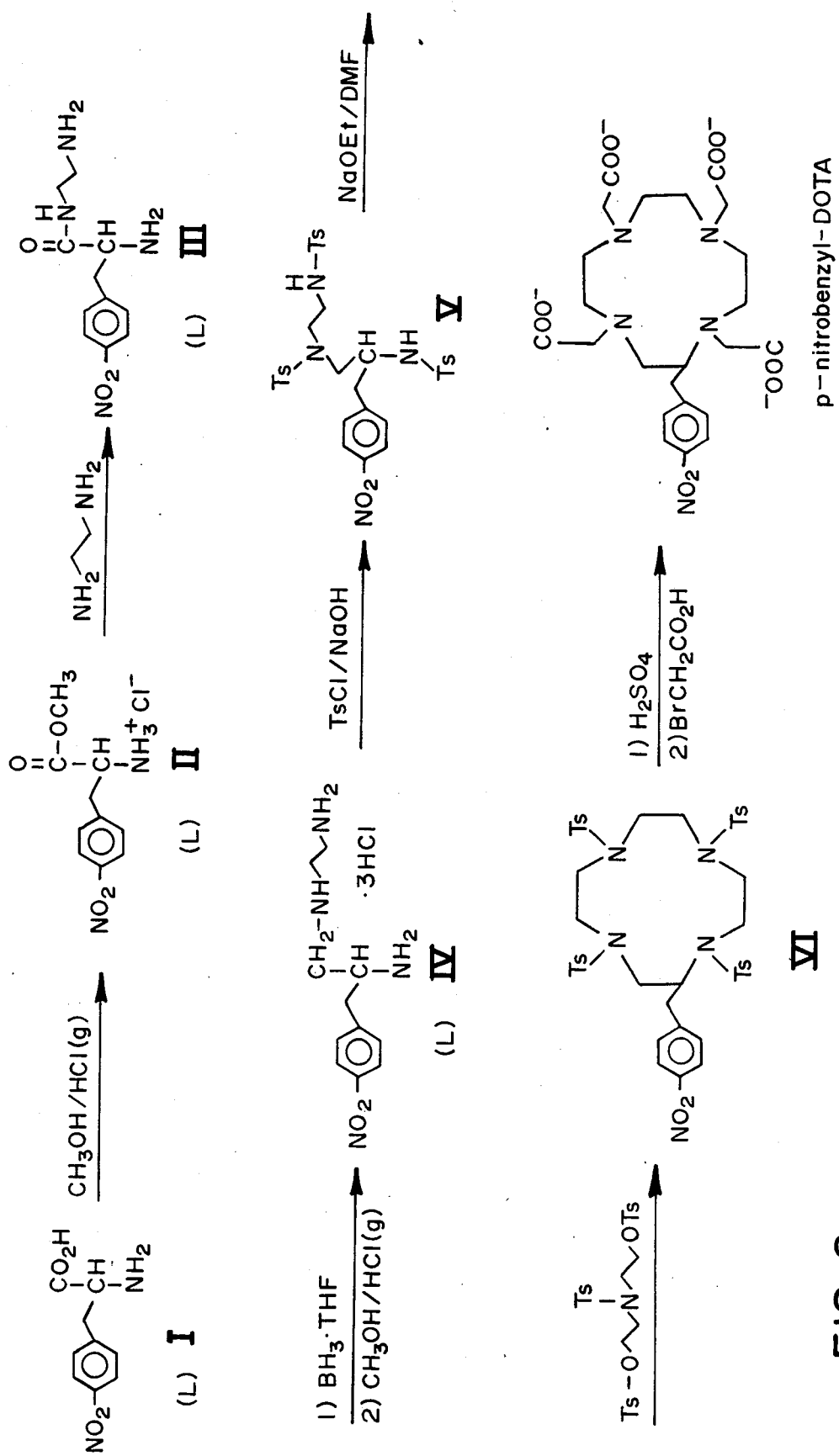
FIG. 2 shows a series of reactions used in synthesizing another bifunctional chelate for use in the invention.

FIG. 2 shows a reaction scheme for synthesizing the corresponding macrocyclic tetraaza bifunctional chelating compound in which k, l, m and n=2, i.e., the 12(ane)$N_4$ compound. As a first step, p-nitrophenylalanine (I) is dissolved in methanol, saturated with HCl gas, and allowed to sit for about 2 days at room temperature. The volume of methanolic solution is then reduced and the methyl ester (II) is collected as a precipitate. The ester (II) formed is dissolved in dry methanol, and to this solution is added a large excess of ethylenediamine. The mixture is stirred for about 4 days. After adding water to the mixture, the amide product (III) is extracted with benzene, then dried.

The triamine compound (IV) is formed by adding a solution of 1M borane in THF dropwise to a stirred mixture of the amide in THF, to a final mole ratio of about 7:1, borane:amide, at room temperature. The material is refluxed for 24 hours, followed by addition of methanol at 0° C. After saturating the material with HCl gas, the volume is reduced, and the solid triamine hydrochloride salt that is formed is collected.

A solution of tosyl chloride (TsCl) in ether is added dropwise into a vigorously stirred solution of the triamine compound (IV) in aqueous NaOH at room temperature, to a final mole ratio of TsCl to triamine of about 3:1. The resulting mixture is stirred for 2 hours at room temperature. After decanting the excess aqueous ether layer, the tosylamine compound (V) is isolated on a silica gel column, using a petroleum ether/acetone step gradient. The method follows reference 26.

A cyclic tetratosylamine (VI) is prepared following the general procedures of reference 27. To a hot, stirred mixture of the tosylamine (V) in ethanol is added first, 2 equivalents of sodium ethoxide. Then 1 equivalent of N,O,O'-Tris(p-toluene-sulfonyl)bis(2-hydroxyethyl)amine in DMF is added to the mixture over a 1–2 hour period at 100° C. The product that forms on addition of water at 0° C. is collected.

The tosylated compound (VI) is converted to the corresponding cyclic tetraamine by cleavage in 97% sulfuric acid, followed by work-up with 6M HCl, and the detosylated tetraamine is then converted to a tetraacetic acid by adding to a stirred aqueous solution of the compound at 60° C., pH 7.0, about 5 equivalents of bromoacetic acid. After increasing the temperature to 70° C., and the pH to 11, the mixture is stirred for 1 day, then acidified to pH 3. The 12(ane)$N_4$ chelate moiety of the compound which forms is also referred to as 1,4,7,10-tetraazacycloDOdecane-N',N'',N''',N''''-tetraacetic Acid (DOTA), and the p-nitrobenzyl bifunctional compound, as p-nitrobenzyl-DOTA.

The macrocyclic chelate moiety of the invention, as exemplified by the above DOTA, TRITA, TETA, and HETA ring structures, is characterized by four ring amines disposed in a substantially ring-symmetric configuration, i.e., at substantially four equally spaced intervals about the macrocyclic ring. This arrangement provides a favorable chelation configuration for Cu(II), which can form four coordinate bonds with the amine nitrogens. At the same time, Cu(II) can form two additional coordinate bonds with two acetic acid groups carried on the ring nitrogens.

FIG. 3 shows the three dimensional structure of a Cu(II) chelate of p-nitrobenzyl-TETA, determined by X-ray crystallography. As seen the Cu(II) atom forms two relatively short bonds with one opposite-side pair of ring nitrogens and two relatively long bonds with the other opposite-side pair. The short and long bonds are approximately 2.0 and 2.4 Å, respectively. The two acetate groups which are coordinately bonded to the Cu(II) atom are located on opposite-side nitrogens, and coordinate to the metal in a trans configuration.

The FIG. 3 structure illustrates the protective environment which is provided by the nitrogen and carboxyl-group ligands in the macrocyclic polyamine chelate compounds of the general type described above. Preferred compounds—that is, those considered most favorable for forming the coordinate bonds seen in FIG. 3, are those in which (a) the macrocycle ring structure has k, l, m, and n in values of 2 or 3, and (b) the two bonding acetate groups are located on opposite-side ring nitrogens. Although only two carboxyl groups are required for Cu(II) complexing, the presence of acetate groups on all four ring nitrogens provides the advantage that a variety of other metals, such as indium, terbium, europium, gadolinium, and also iron and cobalt, which form stable complexes with tetraacetic acid chelators can also be complexed with the compound. The conjugate of the invention can then be used for therapeutic or diagnostic applications involving metals other than Cu(II). Preferred tetraacetic acid macrocyclic polyamine compounds include the DOTA, TRITA, TETA, and HETA compounds described above.

Copper(II), either nonradioactive Cu(II), or radioactive $^{64}$Cu(II) or $^{67}$Cu(II), can be complexed with the bifunctional chelate compound, by adding the compound to a solution of a copper salt (e.g., copper nitrate). Copper chelates of p-nitrobenzyl-TETA form readily upon mixing in an aqueous solution at neutral pH. When necessary, copper-chelate formation may be carried out at elevated pH and/or temperature. Copper may also be complexed with the macrocyclic chelate after the bifunctional chelating compound is conjugated to a biomolecule. However, studies conducted in support of the invention indicate that with relatively short conjugate linkers (less than about 8 atoms chain length), the yield of bound copper is typically lower than if the copper is first complexed to the unconjugated bifunctional compound; that is, best results for attaching copper to a chelate/biomolecule conjugate are obtained if the linker separating the biomolecule from the chelate moiety is at least about 8 atoms in length. Methods for coupling the chelating compound to a biomolecule, to achieve a desired length linker are discussed in Section II.

II. Coupling the Bifunctional Compound to a Biomolecule

The biomolecule to be coupled to the bifunctional compound is typically one selected to carry out a specific target function and/or to prevent rapid renal clearance of the conjugate. In one embodiment, the biomolecule is a monoclonal antibody or antibody fragment which is specific against a selected cell-surface target site. Such antibodies may be commercially available, or may be made by somatic cell hybridization techniques described originally by Kohler and Milstein (reference 16) and reviewed at length in reference 17. Other serum proteins, such as serum albumin, may also be used advantageously in metal-chelate conjugates for tumor localization and in radioimaging (reference 9).

Serum proteins can be coupled to the bifunctional chelating compound through carboxyl or amine groups present on the native protein. Alternatively, in the case of antibody or antibody fragments, the protein can be reduced prior to conjugation, for example, with a sulfhydryl reagent, to form antibody fragments having free sulfhydryl groups. If the linker group in the bifunctional compound reacts directly with the protein (or a reduced sulfhydryl group thereof), the length of the linker is just that of the linker group. To form a linker whose length is greater than that of the linker group the protein can be derivatized with a reagent which itself will contribute to the linker when chemically coupled to the linker group. Example III below describes a method for coupling p-bromoacetamido-TETA to antibody, using the protein-reactive reagent 2-iminothiolane to form a relatively long linker.

The biomolecule in the conjugate may also include bleomycin, an anti-tumor antibiotic which is known to localize selectively within many types of tumors (references 18 and 19). One of the inventors has previously described a class of bleomycin-chelate compounds that can form stable metal chelate with a variety of metals (references 6 and 7). To prepare a compounds of this type, an $A_2$ form of bleomycin is demethylated to produce a thioether which can then react with a suitable reactive group in the bifunctional compound's linker group as described below in Example IV.

Typically, the bifunctional compound is conjugated to the selected biological molecule by first activating the linker group. A variety of known activation reactions suitable for use with a nitrobenzyl linker group are illustrated in FIG. 4. As seen, the nitro group is first reduced, for example, by catalytic hydrogenation, to produce the p-aminobenzyl chelate (II). The latter compound may be converted to isothiocyanate (III) by treatment with thiophosgene. The isothiocyanate may be directly reacted with proteins for coupling via a thiourea linkage. This coupling method is described in reference 5.

In another preferred reaction, the amine is acylated with a reagent such as bromoacetylbromide, to form the reactive bromoacetamide group shown at IV in FIG. 4. The bromoacetamide linker group in the compound readily alkylates free proteins, to form the desired protein/chelate conjugate, as described in Example II. Alternatively, where it is desired to form an extended-length linker the protein may first be reacted with a reagent, such as 2-iminothiolane, which, when derivatized to the protein, provides a spacer chain that terminates at a suitable end-group, such as a sulfhydryl group. The bromoacetamide compound, when reacted with protein, combines with the spacer chain end-group to form the extended linker. This coupling method is illustrated in Example III.

The bromoacetamide bifunctional compound (IV) also reacts readily with the thioether group formed by demethylating bleomycin $A_2$, as described above, to couple the bifunctional compound to bleomycin through a sulfonium bond. Example IV below describes the synthesis of a bleomcyin-TETA conjugate by this method.

Nitrous acid treatment of compound II yields the diazonium ion (V) which reacts readily with tyrosine, histidine and lysine groups in proteins, to derivatize proteins through a diazo bond (reference 9). Finally, the biological molecule itself may have an amine-reactive group, such as an acid halide group, through which the amine can be coupled directly to the molecule, as indicated at VI in the figure.

III. Conjugate Stability in Human Serum

This section examines the rate of loss of copper from a bifunctional macrocyclic copper chelate compound and conjugate in human serum under substantially physiological conditions. The studies described herein show that the rate of loss of copper from a cyclic tetraazatetraacetic acid bifunctional chelate compound or conjugate formed in accordance with the invention is less than about 1% per day in human serum, in contrast with chelating agents that have been used in the prior art, which show much higher rates of copper loss in human serum.

The copper stability of the six copper chelate compounds listed in Table I below was investigated. Compound #1 is an N-butylamide dieethylenetriaminepentaacetic acid (DTPA) bifunctional compound prepared as described in reference 19. To produce compound #2, the DTPA cyclic anhydride was conjugated with mouse monoclonal antibody by a standard procedure (reference 12). Compound #3 is a nitrobenzyl-ethylenediaminetetraacetic acid (EDTA) bifunctional compound prepared as described in reference 5. The bifunctional EDTA compound was converted to the isothiocyanate and attached to mouse monoclonal antibody according to the method described in reference 5. The nitrobenzyl-TETA compound (#5) was prepared as in Example I, and the Cu-benzyl-TETA antibody conjugate (#6), as described in Example II. Copper chelates of compounds number 1, 3, and 5 were prepared by mixing each chelator, at a concentration of about $10^{-3}$M for #1 or $10^{-5}$M for #3 and #5, with "carrier-free" [$^{67}$Cu] CuCl$_2$ in aqueous solution, at a pH adjusted to 7 using 0.1M NaOH. For the p-nitrobenzyl-TETA and p-nitrobenzyl-EDTA compounds, unchelated copper was removed by passing small aliquots of these solutions through a 0.3 ml CHELEX column a 1 ml tuberculin syringe. This procedure could not be used for compound #1 because CHELEX removed practically all of the copper from the solution.

Copper was added to the antibody conjugates of DTPA and EDTA by incubating the conjugate (about $10^{-4}$M conjugate) with "carrier-free" [$^{67}$Cu] CuCl$_2$ in 0.1M sodium acetate, pH 5.5–7.5. A standard analysis was performed to confirm copper chelation (reference 5). In forming the TETA copper conjugate, the antibody was conjugated to the copper chelate as described in Example I. For all three compounds the radiolabeled conjugate was isolated by centrifugation through Sephadex G-50.

Serum was prepared from blood collected from human volunteers, by allowing the blood to clot for 1 hr, centrifuging at approximately $4 \times g$ and filtering the serum through a 0.2 micron syringe filter into sterile plastic culture tubes. Serum pH was checked immediately prior to use and was always 7–7.1.

Each experimental sample consisted of 1.5–2.0 ml of serum and 100 $\mu$l of radioactive chelate solution (1–10 $\mu$Ci). The initial concentration of radiolabeled chelate in the serum was approximately 10 $\mu$M, except for compound 1 which was about 1 mM. The sample solutions were incubated at 37° in a humidified chamber maintained in 5% $CO_2$, 95% air throughout the several-day period.

Ten $\mu$l aliquots of the serum mixtures were analyzed by HPLC gel filtration (TSK 3000 column, Beckman) and cellulose acetate electrophoresis. Radioactive profiles obtained from HPLC fractions were compared to the UV absorbance profiles. The cellulose acetate electrophoresis strips were cut in half lengthwise, and one half was stained with Coomassie brilliant blue (0.25% in water). The other side was counted for radioactivity distribution by cutting the strip into 0.3 cm sections and counting the sections in an automatic well counter. The radioactive distribution was compared to the positions of the stained protein bands. Results of the HPLC and electrophoresis were always in good agreement. The percent of $^{67}$Cu remaining in each chelate as a function of incubation time at days 0, 3, and 5 is shown in Table I.

TABLE I

| No. | Chelate | % of Cu Remaining DAY | | |
|---|---|---|---|---|
| | | 0 | 3 | 5 |
| 1 | DTPA-NBu ($10^{-3}$ M) | 100 | 35 | 33 |
| 2 | DTPA-antibody (~$10^{-5}$ M) | 100 | 6 | 5 |
| 3 | EDTA-NO$_2$ benzyl (~$10^{-5}$ M) | 95 | 18 | 18 |
| 4 | EDTA-antibody (~$10^{-5}$ M) | 94 | 4 | 5 |
| 5 | TETA-NO$_2$ benzyl (~$10^{-5}$ M) | 100 | 98 | 98 |
| 6 | TETA-antibody (~$10^{-5}$ M) | 100 | 96 | 94 |

The table shows that copper chelates of EDTA or DTPA are not stable to prolonged incubation in human serum. This is true both for antibody conjugates and for the two low-molecular weight bifunctional compounds. In fact, these four compounds apparently reached equilibrium in a few hours.

Both copper chelates of TETA are stable in serum, was evidenced by a 94–98% retention of copper after five days incubation. It is interesting to note that available equilibrium constants for the copper chelates of EDTA, DTPA and TETA (references 14, 15, and 21) imply that, at pH 7.0, TETA-Cu(II) is the *least* stable. Thus the observed stability of the copper chelate of the two TETA compounds cannot be ascribed to a more favorable equilibrium position.

The overall rate of loss of copper from nitrobenzyl-TETA (or the antibody conjugate) in serum is about 1% per day. This rate of loss of copper is slow enough to be acceptable for practically all applications of this chelate as a biological probe or therapeutic agent. One application of the copper-chelate conjugate of the invention is for use in radioimaging. It has been established by one of the inventors and others that a variety of metal chelates, when conjugated with serum proteins, target-specific antibodies, or bleomycin can be localized in tumor or other target tissue to provide useful radioimaging images used in localizing tumors (references 5-10). In this application, a copper chelate of the conjugate is injected in a patient and allowed to localize in a tumor region(s). These regions are imaged using radioimaging equipment such as a γ photon emission tomograph or a positron emission computed tomograph. Various strategems may be employed to enhance the image contrast which is achievable. For example, with a chelate conjugate formed with a serum protein, the image contrast can be improved by administering an anti-conjugate antibody following tumor uptake of the conjugate, to increase the rate of clearance of the conjugate from the bloodstream (reference 10).

The stable Cu(II) bifunctional compound, or conjugate is also suitable for use as a therapeutic agent, based either on the radiotherapeutic action of $^{67}$Cu, for example when localized in tumor tissue, or on the cytotoxic effects producible by non-radioactive copper chelates. The latter effects involves oxidative cell damage, such as DNA nicking, and have been shown, in the case of iron chelates, to potentiate the cytotoxic action of radiation on cells. The conjugate containing paramagnetic Cu(II) in stable form is also expected to provide a useful adjunct to NMR imaging techniques.

From the foregoing, it can be appreciated how various objects and features of the invention are met. The conjugate of the invention provides a chelated form of copper which is stable in human serum and therefore suitable for therapeutic and diagnostic applications which involve copper localization via the systemic route. The conjugate may be formed with one of a variety of biomolecules for specific targeting to tumor and/or other tissue having surface-specific features.

The following examples illustrate various aspects of preparing the conjugate of the invention, but are in no way intended to limit the scope thereof.

EXAMPLE I

Preparing p-Nitrobenzyl-TETA

Diethyl malonate was purchased from Sigma Chemical Co. (St. Louis, MO) and redistilled before use; p-nitrobenzyl bromide and borane-tetrahydrofuran (1.0M) were obtained from Aldrich (Milwaukee, WI); bromoacetic acid (Aldrich) was recrystallized from hexane before use; and N,N'-bis(2-aminoethyl)-1,3-diaminopropane was from Eastman (Rochester, NY). Water was doubly deionized and distilled. $^{67}$Copper chloride was obtained from Dr. H. A. O'Brien, Los Alamos National Laboratory.

Alkylation of diethyl malonate with p-nitrobenzyl bromide was carried out under anhydrous conditions (reference 23). Sodium ethoxide was generated by dissolving 0.1 mole sodium metal in 100 ml of dry ethanol. Next, diethyl malonate (0.2 mole) was added dropwise at room temperature, followed by the addition of p-nitrobenzyl bromide (0.1 mole). The reaction mixture was refluxed for 24 hours, and precipitated side products were removed by filtration. The product was crystallized by slowly evaporating the ethanol from the filtrate: yield 63%. Characterization of the product (I in FIG. 1) was done by TLC (silica gel developed in CHCl$_3$, Rf 0.56), IR (1725 cm$^{-1}$ (s) carbonyl), m.p. 58°-60° C. (lit. 58°-60° C.), and proton NMR (in CDCl$_3$: t, 1.15, 6H; d, 3.25, 2H; m, 3.60, 1H; m, 4.15, 4H; d, 7.35, 2H; d, 8.15, 2H; chemical shifts relative to CHCl$_3$, 7.24).

The alkylated diethyl malonate from above (0.0637 mole) was refluxed with N,N'-bis(2-aminoethyl)-1,3-diaminopropane (0.0637 mole) in 1274 ml of ethanol for 4 days (reference 13). After reflux, the excess ethanol was removed under reduced pressure and the crystals formed were collected by filtration. Additional product was obtained by purifying the filtrate using a silica gel column (J. T. Baker, 60-200 mesh, 4 cm×40 cm), which had been partially deactivated by running 400 ml of H$_2$O-saturated CHCl$_3$ through it. Application of the sample was followed by step elution with 800 ml CHCl$_3$:MeOH (3:1), 400 ml CHCl$_3$:MeOH (2:1), and 400 ml CHCl$_3$:MeOH (1:1) mixture: overall yield 14%. Characterization of compound II (FIG. 1) was done by TLC (silica gel developed (12) in MeOH:CHCl$_3$:conc. NH$_4$OH (2:2:1), Rf 0.54), and proton NMR (D$_2$O/DCl, pH 5: m, 2.9-3.9, 15H; d, 7.45, 2H; d, 8.15, 2H; chemical shifts relative to HDO, 4.64).

The cyclic diamide (1.62 mmoles) was treated under reflux for 5 hours with borane (16.2 mmoles) in 50 ml of dry tetrahydrofuran. Then 50 ml of methanol was added in small aliquots to the reaction mixture, followed by saturation with HCl gas and 1 hour reflux. After volatile components were removed under reduced pressure, the cyclic tetramine hydrochloride (III in FIG. 1) was collected and recrystallized in ethanol; yield 58%. Characterization was done by TLC (silica gel developed in CHCl$_3$:MeOH:conc. NH$_4$OH (2:2:1), Rf 0.06), and proton NMR (in D$_2$O, pH 1: m, 2.1, 2H; m, 2.65-3.75, 19H; d, 7.40, 2H; d, 8.10, 2H).

The final step, involving carboxymethylation of the cyclic tetraamine, was carried out in glassware which was acid-washed to remove trace metals. Bromoacetic acid (2.28 mmoles) was added to a stirred solution of the cyclic tetraamine from above (0.457 mmole) in distilled water at 75° C., pH 10. The pH was maintained by addition of saturated KOH. After stirring for 24 hours at 75° C., the reaction was cooled to room temperature and the pH was adjusted to 3.4 with 7M formic acid. At this point p-nitrobenzyl-TETA (IV in FIG. 1) was observed to precipitate. After several washings at pH 3 and centrifugation, the precipitate was dried and collected: yield 11.6%. Characterization was done by FAB-MS (m/e 568, m+1), $^{13}$C NMR (in D$_2$O/NaOD, pH 12, fully decoupled: 21.669; 26.440; 36.928; 47.814; 48:981; 50.333; 57.174; 58.529; 59.272; 123.231; 129.947; 145.576; 149.563; 178.315; 178.771; chemical shifts relative to dioxane, 66.500), and proton NMR (in D$_2$O/NaOD, pH 12: m, 1.50, 2H; m, 2.45, 19H; s, 2.90, 8H; d, 7.40, 2H; d, 8.05, 2H). The predicted $^{13}$C nmr spectrum was in good agreement with the observed spectrum.

The copper(II) chelate of p-nitrobenzyl-TETA was formed by mixing the chelator (about 10$^{-3}$M) with CuCl$_2$ (about 10$^{-3}$M) in aqueous solution, with the pH adjusted to 7 using 0.1M NaOH. The copper chelate has a visible absorbance maximum at 632 nm (pH 7, H$_2$O);

and it elutes from an anion-exchange column at approximately the same position as copper-EDTA, confirming that it also carries a charge of −2.

EXAMPLE II

Conjugation to Antibody

Lym-1, an IgG$_{2a}$ mouse monoclonal antibody against B-cell lymphoma, was obtained from Dr. Alan L. Epstein, Northwestern University, Evanston, IL.

The aromatic nitro group of Cu-p-nitrobenzyl-TETA from Example I was converted to a reactive bromoacetamide using the methods of Meares et al (reference 5). The reaction mixture was extracted with ethyl ether to remove unreacted bromoacetylbromide and the activated chelate compound was lyophilized. A solution of the antibody (0.5 mM) and chelate compound (1.5 mM) in 0.15M sodium phosphate, pH 8.0, was prepared. The mixture was adjusted to pH 9.0–9.5 with saturated trisodium phosphate, and incubated at 37° C. for 2 hr. The reaction mixture was applied to a Sephadex G-50-80 column, to remove free chelate compound.

EXAMPLE III

Conjugation to Antibody Through An Extended Chain

Mouse monoclonal antibody (Example II) was reacted with 2 mM 2-iminothiolane for 45 minutes at 4° C., to derivatize antibody amino groups (Ab-NH):

The protein was freed from unbound 2-iminothiolane, then reacted with the bromoacetate bifunctional TETA compound used in Example II, except that the compound was not chelated with copper prior to conjugation with the antibody. The conjugate formed has the following structure:

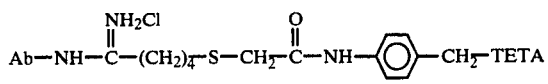

The conjugate was considerably easier to radiolabel with metal ions, including Cu(II) and Co(II), than the shorter-spacer antibody/chelate conjugate formed in Example II.

EXAMPLE IV

Conjugation to Bleomycin

Demethylated bleomycin A$_2$ (A$_2$Dm) is prepared as in reference 7. CO(III)-bleomycin A$_2$DM (6.18 μmole) and 61.8 μmol p-bromoacetamidobenzyl-TETA are combined in an aqueous solution in a final volume of 1.87 ml. The pH of the solution is adjusted to 4.4 by the addition of NaOH. The reaction is allowed to proceed at room temperature and was monitored by HPLC. After 6 hours, the pH of the reaction mixture is adjusted to 8.2 and the mixture applied to a Sephadex A-25 column. The product is eluted with a 500 ml gradient of 0.01M to 0.3M NH$_4$O$_2$CH, pH 8. The absorbance at 452 nm of every other fraction is determined. Fractions containing the product are pooled and lyophilized for 2 days to remove solvent and excess salt.

While preferred embodiments and uses of the present invention have been described herein, it will be apparent that various other embodiments and modifications fall within the scope of the invention.

It is claimed:

1. A copper chelate conjugate for diagnostic or therapeutic applications which involve Cu(II) localization via the systemic route, comprising:
a Cu(II) chelate of a bifunctional macrocyclic polyamine having the form:

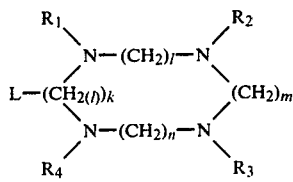

where k, l, m, and n = 1–4, and at least two of R$_1$–R$_4$ are —CH$_2$CO$_2$$^-$ acid groups, the remainder are —CH$_2$CO$_2$$^-$ or —H, L is a linker attached at one end to a ring carbon in the polyamine, and having at its other end, a chemically reactive group capable of reacting with a biomolecule, to form a chemical linkage therewith, and CH$_{2(1)}$ indicates that the ring carbon to which the linker is attached has only one hydrogen, and
chemically linked to the linker, a biomolecule selected from the group consisting of antibodies, antibody fragments, serum proteins, and bleomycin.

2. The conjugate of claim 1, wherein at least two —CH$_2$CO$_2$$^-$ acid groups are located on diagonally opposite nitrogens in the macrocyclic polyamine.

3. The conjugate of claim 1, wherein the macrocyclic polyamine is selected from the group consisting of 1,4,7,10-tetraazacycloDOdecane-N',N",N''',N''''-tetraacetic Acid (DOTA); 1,4,7,10-tetraazacyclo-TRIdecane-N,N',N",N'''-Tetra-acetic Acid (TRITA); 1,4,8,11-tetraazacyclo-TEtra-decane-N,N',N",N'''-Tetraacetic Acid (TETA); and 1,5,9,13-tetraazacyclo HExa decane-N,N',N",N'''-Tetraacetic Acid (HETA).

4. The conjugate of claim 1, wherein the linker is at least 8-atoms in length.

5. A method of preparing Cu(II) for use in diagnostic and therapeutic applications which involve Cu(II) localization via the systemic route, comprising
preparing a bifunctional polyamine macrocycle having the form:

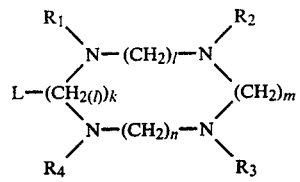

where k, l, m, and n = 1–4, and at least two of R$_1$–R$_4$ are —CH$_2$CO$_2$$^-$ acid groups, the remainder are —CH$_2$CO$_2$$^-$ or —H, L is a linker attached at one end to a ring carbon in the polyamine, and having at its other end, a chemically reactive group capable of reacting with a biomolecule, to form a chemical linkage therewith, and CH$_{2(1)}$ indicates that the ring carbon to which the linker is attached has only one hydrogen, and
reacting the linker with a biomolecule selected from the group consisting of antibodies, antibody fragments, serum proteins, and and bleomycin, under conditions which are effective to couple the biomolecule covalently to the free end of the linker group, to form a macrocycle/biomolecule conjugate; and adding a Cu(II) salt to the macrocycle, prior to or after said reacting, to form a copper chelate of the macrocycle.

6. The method of claim 5, wherein the macrocycle is a tetraacetic acid.

7. The method of claim 5, wherein the linker has a free-end nitro group, and said reacting includes reducing the nitro group to an amine, activating the amine to form a reactive chemical group, and coupling the reactive compound with the biomolecule.

8. The method of claim 5, wherein the biomolecule and macrocycle are separated by a spacer of less than about 8 atoms in length, and said adding is done prior to said reacting.

9. The method of claim 5, for preparing Cu(II) for use in treating a tumor, wherein the chelate formed is a $^{67}$Cu chelate of the cyclic compound.

10. The method of claim 5, for preparing Cu(II) for radioimaging, wherein the chelate formed is a $^{64}$Cu chelate of the cyclic compound.

11. The use of a bifunctional cyclic tetraaza di-, tri-, or tetra-acetic acid copper chelate compound of the form:

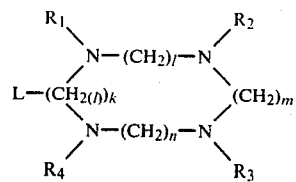

where k, l, m, and n=1–4, and at least two of $R_1$–$R_4$ are —$CH_2CO_2^-$ acid groups, the remainder are —$CH_2CO_2^-$ or —H, L is a linker attached at one end to a ring carbon in the polyamine, and having at its other end, a chemically reactive group capable of reacting with a biomolecule, to form a chemical linkage therewith, and $CH_{2(l)}$ indicates that the ring carbon to which the linker is attached has only one hydrogen, for diagnostic and therapeutic applications which involve Cu(II) localization via the systemic route.

12. The use of claim 11, wherein the compound is conjugated to a biomolecule selected from the group consisting of antibodies or antibody fragments, serum proteins, and bleomycin.

13. The use of claim 11, for tumor localization applications, wherein the chelate compound is a $^{64}$Cu chelate.

14. The use of claim 11, for tumor radiotherapy application, wherein the chelate compound is a $^{67}$Cu chelate.

* * * * *